(12) United States Patent
Fregoso-Infante et al.

(10) Patent No.: US 7,893,122 B2
(45) Date of Patent: Feb. 22, 2011

(54) CHEMICAL PROCESS FOR RECYCLING POLYETHYLENE TEREPHTHALATE (PET) WASTE

(76) Inventors: Arturo Guadalupe Fregoso-Infante, Playa Langosta No. 162, Col. Marte, Deleg. Iztacalco (MX) 08830; Roxana Vega-Rangel, Leopoldo Beristain No. 19, Cd. Statelite, Circuito Actores (MX) 53100; Maricruz Figueroa-Gomez-Crespo, Uxmal No. 26, Col. Navarte (MX) 03020

( * ) Notice: Subject to any disclaimer, the term of this patent is extended or adjusted under 35 U.S.C. 154(b) by 383 days.

(21) Appl. No.: 10/587,518

(22) PCT Filed: Jan. 27, 2004

(86) PCT No.: PCT/IB2004/000257

§ 371 (c)(1),
(2), (4) Date: Mar. 2, 2007

(87) PCT Pub. No.: WO2005/082826

PCT Pub. Date: Sep. 9, 2005

(65) Prior Publication Data

US 2007/0219339 A1 Sep. 20, 2007

(51) Int. Cl.
*C08J 11/04* (2006.01)

(52) U.S. Cl. ............... 521/48.5; 521/40; 521/40.5; 521/47; 521/48; 528/271; 528/272; 528/480; 528/488; 528/489; 528/495; 528/499; 528/502 R; 528/502 A; 528/503

(58) Field of Classification Search ........... 521/48.5, 521/40, 40.5, 41, 41.5, 42, 42.5, 48, 47; 528/271, 528/272, 480, 488, 489, 495, 502 R, 503; 428/480
See application file for complete search history.

(56) References Cited

U.S. PATENT DOCUMENTS 3,801,273 A * 4/1974 Mays .................... 8/141
6,580,005 B1 6/2003 Yazaki et al.

FOREIGN PATENT DOCUMENTS

GB 822834 A 11/1959

OTHER PUBLICATIONS

Hu, L.-C. et al. Alkali-Decomposition of Poly(ethylene terephthalate) in Mixed Media of Nonaqueous Alcohol and Ether. Study on Recycling of Poly(ethylene terephthalate). Polymer Journal, 1997, vol. 29 N 9, paginas 708-712.
Katayannidis, G.P. et al. Poly(ethylene terephthalate) Recycling and recovery of pure Terephthalic Acid by Alkaline Hydrolysis, Advances in Polymer Technology, 2002, vol. 21, N 9, paginas 250-259.

* cited by examiner

*Primary Examiner*—Ling-Siu Choi
*Assistant Examiner*—Frances Tischler
(74) *Attorney, Agent, or Firm*—Browdy and Neimark, PLLC

(57) ABSTRACT

The present invention relates to a process for chemical recycling of PET waste that comprises, among other stages, a saponification reaction stage, wherein PET waste particles are reacted with stoichiometric or excessive amounts of a strong base metal in an alcoholic reaction media, the reaction being brought to the boiling temperature of the alcoholic reaction media, preferably at atmospheric pressure, thereby obtaining as reaction products a salt of terephthalic acid with the base metal and ethylene glycol, the latter being incorporated to the alcoholic reaction media. From this reaction it is possible to afford ethylene glycol, terephthalic acid and salts thereof, which are products with a high commercial value.

9 Claims, No Drawings

CHEMICAL PROCESS FOR RECYCLING POLYETHYLENE TEREPHTHALATE (PET) WASTE

FIELD OF THE INVENTION

The present invention relates to techniques employed in the chemical industry for the recovery of chemical products from polymeric waste materials and, particularly, to a chemical recycling process of polyethylene terephthalate (PET) wastes.

BACKGROUND OF THE INVENTION

Nowadays, polyesters are widely used in several products for human consumption, among which polyethylene terephthalate, better known as PET—saturated polyester from terephthalic acid and ethylene glycol—is one of the best known.

In recent years, PET consumption has especially soared since such compound is extensively employed in the manufacturing of containers for diverse liquid products, such as water and other bottled beverages. It is estimated that worldwide PET consumption adds up to more than 13 million tons distributed in three mayor markets, i.e. the textile, video tape and packing and container industries, the latter mainly comprising the manufacturing of bottles for beverages.

In connection thereinbefore, PET has been employed particularly in the manufacture of bottles for beverages due to its low weight, high strength, low permeability to gases and, above all, to the fact that PET has no deleterious effects on human health.

In spite of the advantages hereinabove concerning the use of PET, this material however brings about parallel environmental issues, since PET bottles occupy a large volume once they are disposed of and their degradation takes place quite slowly, given their significant resistance against atmospheric and biological agents. Thus, the PET is currently being classified as a pollutant agent.

As a result of such ecological issues and in tandem with economic concerns, the prior art has contemplated the recycling of PET and other polyesters by means of various techniques and processes, among which that known as "material recycling" is one of the simplest consisting of the collection, cleaning, grinding and granulation of the waste polymer, to incorporate it thereafter to the production of different items that need not comply with high quality and/or purity standards; hence, the field of application of this recycling technique is certainly narrow.

On the other hand, there exists what is known as "chemical recycling" (depolymerization), which comprises breaking the polyester chains. In this regard, an important number of chemical processes to depolymerize PET or other polyesters can be found in the prior art, such processes being classified in four major groups as follows: a) glycolysis, b) alcoholysis, c) hydrolysis and d) saponification.

Regarding glycolysis, it consists of degrading the polyester with diols such as ethylene glycol to temperature conditions from about 1800 to 250° C. When PET is decomposed via this process, the products obtained are mainly bis(hydroxyethyl) terephthalate (BHET) and ethylene glycol (EG) which is incorporated to the reacting media. As shown, one of the drawbacks in glycolysis is that high temperatures are required to perform it, which entails an important consumption of energy at an industrial scale.

One example of glycolysis decomposition may be found in the European Patent Serial No. 1,227,075 A1, which discloses a recovery method of dimethyl terephthalate (DMT) and ethylene glycol from polyester, notably PET. It is worth mentioning that the disclosed method contemplates the use of a depolymerization catalyst of polyesters in ethylene glycol, the reaction taking place at a temperature of from 175° to 190° C. and pressures ranging from 1 to 5 atm (0.1. to 0.5 MPa).

Regarding alcoholysis, polyester is degraded with alcohols, mainly methanol, wherein depolymerization occurs under temperature conditions of from 200° to 300° C. and pressures ranging from 2 to 300 atm; this presents a drawback because of the need of equipments that withstand such pressure. On the other hand, when PET is broken down, the main products obtained with such a process are dimethyl terephthalate (DMT) and ethylene glycol (EG).

A methanolysis process is disclosed in U.S. Pat. No. 5,051,528, wherein PET is dissolved in terephthalic acid and ethylene glycol oligomers, thereafter treated with methanol and obtaining in result DMT and ethylene glycol.

Concerning depolymerization by hydrolysis, it contemplates the rupture of the ester bond by means of OH ions. Likewise, hydrolysis takes into account the following variants:

i) Alkaline or basic hydrolysis, wherein an alkali is employed to break down the polyester, mainly NaOH, in an aqueous media and the reaction takes place under high temperatures and pressures; in other instances, the reaction media is ethylene glycol as well;

ii) Neutral hydrolysis, wherein the reaction takes place with the use of water at elevated temperatures; and iii) Acid hydrolysis, wherein the polyester is broken down via the use of concentrated sulfuric acid.

An example of alkaline hydrolysis is found on European patent Serial No. 0 973 715 B1, wherein PET is heated in an aqueous solution at temperatures ranging from 150° to 280° C. with a reactive agent selected from the group consisting of ammonia bicarbonates and alkaline metals.

Finally, in depolymerization with saponification, PET is molten down to treat it with strong bases such as potassium or sodium hydroxides at temperatures above 200° C.

Regarding the above, reference is made to the PET depolymerization process disclosed in U.S. Pat. No. 6,580,005 B1, which provides a process aimed at overcoming the disadvantages of traditional PET depolymerization processes. Particularly, such document discloses a method to recover terephthalic acid from ground PET waste, which method comprises (a) a decomposition reaction step, wherein ground PET waste undergoes a continuous decomposition reaction in ethylene glycol and in the presence of an alkali in an equimolar or excess ratio to PET, such that the salt of terephthalic acid and ethylene glycol can be afforded continuously; (b) a solid-liquid separation step, dissolution and removal of impurities, wherein ethylene glycol is separated from the terephthalic acid salt stemming from the decomposition reaction of terephthalic acid and ethylene glycol, and the terephthalic acid salt is dissolved in water, whereas insoluble impurities are removed; (c) a neutralization/crystallization step, wherein the solution of said terephthalic acid salt is neutralized with acid such that the terephthalic acid can be crystallized; (d) a washout/solid-liquid separation step, wherein the mass of terephthalic acid crystals undergoes a solid-liquid separation such that terephthalic acid crystals can be obtained and washed; and (e) a drying/grinding stage, wherein terephthalic acid crystals are washed, dried and ground.

From the process hereinabove it should be noted again that elevated temperatures are required in the decomposition reaction step, particularly in the ranger of from 130° and 180° C. and, as perceived in the examples included in the application, temperatures in the range of 180° C. to 190° C. must be achieved to favor the breaking of PET chains. Likewise, it is important to point out that prior to decomposition reaction a preheating stage is contemplated wherein ground PET is heated to temperatures ranging from 100° to 140° C., or a thermal degradation at temperatures ranging from 290° C. to 330° C. From the latter, it is noted that high temperatures must be achieved as well in these prior stages.

Another major drawback of the above process is the use of sodium carbonate as the alkali employed in the decomposition reaction, since this compound gives off carbon dioxide during the decomposition reaction, thereby increasing the reactor pressure; accordingly, this equipment must de designed to withstand such pressurization conditions.

In a nutshell, the chemical decomposition processes known in the prior art pose important disadvantages, particularly in the sense that such processes include a depolymerization reaction stage conducted at elevated temperatures and/or pressures, which in turn render them unattractive from an economic viewpoint due to their high energy consumption or because they require equipments that withstand high pressures. As a consequence, there is a major need of developing processes that, in addition to their efficacy, can also be appealing economic-wise.

As a result of the above, efforts have been made to overcome the obstacles posed by prior art chemical PET decomposition process through the development of a chemical recycling process of PET waste, the process including a depolymerization reaction stage (saponification) conducted at lower temperatures than those of prior art depolymerization reaction processes, such saponification stage being additionally carried out at atmospheric pressure or above. The products recovered under such process can be employed as starting material.

SUMMARY OF THE INVENTION

Taking into account the flaws of the prior art, an object of the present invention is to provide a practical and simple chemical recycling process of polyethylene terephthalate PET waste, yet highly efficient in recovering compounds with high commercial value from waste PET, the process including a depolymerization reaction (saponification) stage that is executed under low temperatures and preferably at atmospheric pressure.

An additional object of the present invention is to provide a chemical recycling process of polyethylene terephthalate PET waste which allows obtaining high conversion rates from PET degradation.

A further object of the present invention is to provide a chemical recycling process of polyethylene terephthalate PET waste wherein, after the saponification reaction stage, products such as ethylene glycol, terephthalic acid or salts thereof, can be recovered by means of further stages to the saponification reaction, with the possibility of such recovered compounds of being reusable as starting material.

DETAILED DESCRIPTION OF THE INVENTION

It has been surprisingly found that PET can be depolymerized via a saponification reaction executed at temperatures defined by the boiling point of an alcoholic reaction means, said temperatures being lower in comparison with those disclosed in any prior art depolymerization reactions, said saponification stage being conducted preferably at atmospheric pressure, although higher pressures can be employed as well. A series of stages may follow the saponification reaction with the purpose of recovering ethylene glycol, terephthalic acid or salts thereof, which are compounds with a high commercial value.

Now, the chemical recycling process of polyethylene terephthalate PET waste disclosed in accordance with a particularly specific embodiment of the present invention, which should be constructed as illustrative and not limiting, comprises the stages of:

a) A saponification reaction stage, wherein the PET waste particles are reacted with stoichiometric or excessive amounts of a strong base metal in an alcoholic reaction media, where the reaction is brought to the boiling temperature of the alcoholic reaction media, thereby obtaining as reaction products a salt of terephthalic acid with the base metal and ethylene glycol, the latter being incorporated to the alcoholic reaction media. In a preferred embodiment, the saponification reaction stage is executed at atmospheric pressure, being possible to execute the same at higher pressures than atmospheric pressure.

b) A separation stage of such terephthalic acid salt, wherein the latter is separated from the alcoholic reaction media;

c) A terephthalic acid formation stage, wherein from terephthalic acid salt of stage (b) terephthalic acid is obtained, reacting said salt with a stronger acid than terephthalic acid to form and precipitate the latter as crystals;

d) A solid-liquid separation stage, wherein precipitated terephthalic acid in stage (c) is separated from the media where it was crystallized;

e) An ethylene glycol recovery stage, wherein ethylene glycol and the alcoholic reaction media are separated and recovered from the reaction media separated in stage (b).

Regarding the above process, it should be mentioned that PET waste particles are obtained from any source such as used beverage bottles and package, and it can be in any known shape, i.e. as fiber, film and the like etc.

In the saponification reaction stage, the base employed for reacting with PET is selected from the group consisting of alkaline metal hydroxides or alkaline earth metal hydroxides, being sodium hydroxide (NaOH) or potassium hydroxide (KOH) employed in a preferred embodiment.

Regarding the alcoholic reaction media in which the saponification reaction takes place, said is essentially composed by: a mono- or polyhydric alcohol, a mixture of monohydric alcohols, a mixture of polyhydric alcohols or a mixture of mono- and polyhydric alcohols. In a particular embodiment of the present invention, the alcoholic reaction media is comprised of a monohydric alcohol selected from alcohols with 1-8 primary, secondary or tertiary, lineal or branched carbon atoms or a mixture thereof. In a preferred embodiment, a 20:80 v/v methanol/ethanol mixture is preferably used as alcoholic reaction media.

Regarding the separation stage of terephthalic acid salt, in an alternative embodiment of the chemical recycling process of the present invention, it is contemplated that when the alcoholic reaction media is immiscible in water, such separation stage comprises the following stages: i) cooling the reaction mixture to a temperature below 90° C.; ii) adding sufficient water to the reaction media in order to dissolve the terephthalic acid salt, thereby obtaining two phases, namely an aqueous phase where the terephthalic acid salt is dissolved, and an organic phase that consists of the alcoholic reaction media in which ethylene glycol is incorporated; and iii) a liquid-liquid separation phase, wherein the aqueous phase containing the terephthalic acid is separated from the organic phase. Thereafter, said separated aqueous phase undergoes stage (c) to form terephthalic acid, whereas the separated organic phase undergoes the stage (e) for ethylene glycol recovery.

In another alternative embodiment of the chemical recycling process of polyethylene terephthalate PET waste of the present invention, it is contemplated that when the alcoholic media is miscible in water, the separation stage of the terephthalic acid salt comprises the stages of: i) optionally cooling down the reaction mixture of stage (a) of the saponification reaction; ii) filtering the reaction mixture to separate the crystals of the terephthalic acid salt formed from the alcoholic reaction media where ethylene is incorporated therein; and iii) washing crystals separated with an organic solvent to remove alcoholic media and ethylene glycol residues that might be embedded in the terephthalic acid salt. Thereafter, the separated terephthalic acid salt undergoes the (c) formation stage of terephthalic acid, whereas the alcoholic media where ethylene glycol is incorporated undergoes the (d) recovery stage thereof.

The solvent is selected from methanol, ethanol, acetone, dichloromethane, chloroform or other volatile organic solvents that are miscible with the alcoholic reaction media.

On the other, and concerning the formation stage of terephthalic acid from the terephthalic acid salt that has been separated, the latter is reacted with an acid stronger than terephthalic acid, such as concentrated sulfuric acid or hydrochloric acid until an acidic pH is achieved of the media where this reaction takes place, thereby precipitating terephthalic acid crystals. These crystals are separated later on in stage (d) of solid-liquid separation, preferably through a filtering process and then washed and purified with the various processes known in prior art, thus obtaining terephthalic acid that can be employed as starting material.

It is important to point out that in the chemical recycling process of polyethylene terephthalate PET waste of the present invention, one object contemplated is the recovery of ethylene glycol formed during the saponification reaction and, therefore, once the crystals from the terephthalic acid salt have been separated in stage (b), the alcoholic reaction media where ethylene glycol is incorporated undergoes a distillation process or other processes known in the prior art of liquid-liquid separation, such that once the separation is performed, ethylene glycol and the alcoholic media can be recovered separately, which can be employed again as starting material.

The chemical recycling process of polyethylene terephthalate PET waste of the present invention will now be explained more clearly through the following examples, which are illustrative and do not limit the invention.

Example 1

A PET waste bottle was cut into little pieces, 3 g out of which were placed in a 100 ml round-bottomed flask and were mixed with 1.5 g NaOH flakes and 30 ml octanol. The mixture was heated under constant stirring and maintained at reflux temperature (around 183° C.) for 15 min. Thereafter, the reacting mixture was allowed to cool down and 50 ml water were added to the flask to dissolve the solids present (sodium terephthalate), afterwards the flask content was filtered off to determine the amount of unreacted PET, which in this case was nil. The filtered liquid, one aqueous and one organic phase respectively, were poured in a separation funnel, where both phases were separated. Thereafter, the aqueous phase was added hydrochloric acid concentrate until an acidic pH was achieved, thereby precipitating the terephthalic acid that was filtered off, washed and dried, and the yield in weight of the product obtained was of 96%. The product thus obtained was classified with IR spectroscopy the spectrum thereof being identical to that reported in the literature for terephthalic acid.

Example 2

The procedure of example 1 was repeated, except that 20 ml ethylene glycol were employed in the reaction; once the mixture was heated and kept at a temperature of 183° C. for 5 minutes, it was allowed to cool down and the flask content was filtered off to separate ethylene glycol from sodium terephthalate formed in the reaction. The precipitate (salt) washed with ethanol to recover the ethylene glycol embedded in the precipitate. The sodium terephthalate afforded 3.2 g, which shows a 98% yield. Ethanol was evaporated from the washing liquid to recover ethylene glycol, which was used again.

Example 3

The process of example 1 was repeated, except that 20 ml hexanol were now employed; the mixture was heated and maintained at a temperature of 147° C. for 15 min, and then allowed to cool down. The flask content was filtered off to separate the liquid phase from the sodium terephthalate formed, which was washed with acetone to recover hexanol and ethylene glycol embedded in the precipitate. The salt thus obtained was dissolved in water, without noticing PET waste residues. Acetone was evaporated from the washing liquid to recover hexanol and ethylene glycol.

Example 4

In a round-bottomed flask 1 g PET cut into tiny pieces and 0.5 g NaOH were reacted with the use of 10 ml 1-penthanol as reaction media; the reaction temperature was of 124° C., which was maintained for 10 min. The reaction mixture was treated with 12 ml water to dissolve the white precipitate formed (sodium terephthalate), thereby affording two phases, one organic and one aqueous. Both phases were separated in a separatory funnel, the aqueous phase being filtered thereafter to remove insoluble impurities. Once the aqueous phase was filtered, it was treated with sulfuric acid until a pH of around 2 was achieved, thereby precipitating the terephthalic acid. The white precipitate was filtered off and washed with water and then dried. The weight of the terephthalic acid obtained was 0.83 g, showing a 96% yield.

Example 5

The process of example 4 was repeated, except that 7 ml 1-buthanol was employed in the saponification reaction, which was carried out at 108° C. for 15 min. Once the terephthalic acid was crystallized and dried, 0.83 g of this compound were obtained, i.e. a yield of 96%.

Example 6

In a 500 ml glass reactor 30 g of ground PET waste were reacted with 15 g NaOH in 150 ml 1-propanol at temperature conditions of 89° C. for 15 min under vigorous mechanical stirring. The reacting mixture obtained was filtered off on a filter screen to remove residual particles. The filtered liquid was reacted with concentrated hydrochloric acid to form and precipitate the terephthalic acid. Thereafter the mixture thus obtained was filtered off, recovering the terephthalic acid from the precipitate while 1-propanol and ethylene glycol were recovered from filtrate by distillation. The weight of PET residues was 1.1 g, showing a 96% conversion.

Example 7

1 g PET was cut into tiny pieces, which were reacted for 5 min with 0.5 g NaOH and 7 ml of a 40:60 v/v 1-penthanol/ethanol mixture at a temperature of 78° C. To the reacting mixtures were added 12 ml water to dissolve the precipitate (sodium terephthalate), thereby affording two phases. The resulting mixture was filtered off and the residue washed and dried in order to obtain the degree of conversion of PET. PET residues weighted 0.02 g, showing a 98% conversion. The aqueous phase was treated with sulfuric acid, thereby precipitating the terephthalic acid, which was then filtered off, washed and weighted. Recovery of terephthalic acid from the aqueous solution was over 95%.

Example 8

The process of example 7 was repeated, except that 7 ml ethanol were now used, and the saponification reaction was performed at 73° C. for 15 min. Upon completion of the reaction water was added to dissolve the terephthalic acid salt formed, this mixture was then filtered off to separate unreacted PET, which in this case turned out to be 0.31 g, thereby showing a 69% conversion. Filtrate was then treated with sulfuric acid to recover terephthalic acid.

Example 9

The process of example 7 was repeated again, except that 7 ml methanol were now used at 59° C. for 20 min. Upon completion of the saponification reaction sufficient water was added to dissolve the terephthalic acid salt formed, the flask content was then filtered off to separate unreacted PET residues, which in this case turned out to be 0.25 g, thereby showing a 75% conversion. Filtrate was then treated with sulfuric acid to recover terephthalic acid.

It is important to highlight that the above examples were carried out in Mexico city, which is located at an altitude of 2,240 meters over the sea level, atmospheric pressure being of 550 mm Hg (0.74 atm); therefore, the boiling temperatures of the alcoholic media were below those known for atmospheric pressure conditions of 760 mm Hg (1 atm).

Pursuant to the above, it is noted that the chemical recycling process of PET waste of the present invention allows a chemical decomposition of such compound by means of a saponification reaction performed at lower temperatures than those of prior art depolymerization reactions, and preferably at atmospheric pressure. Likewise, depending on the alcohol employed, yields of up to 96% are obtained. Therefore, it will be evident for anyone skilled in the art that the embodiments of the chemical decomposition process of PET disclosed above are merely illustrative and not limiting examples of the present invention, since various modifications and changes of its details are possible without departing from the scope of the invention.

Even though certain embodiments of the invention have been illustrated and disclosed herein, it is worth mentioning that numerous modifications thereof are possible, such as the choice of alcoholic media, the base employed in the saponification reaction, and pressure under which such reaction takes place, as well as the methods by means of which ethylene glycol, terephthalic acid and salts thereof can be recovered, among others. Therefore, the present invention shall not be regarded as limiting, except for that required by the prior art, as well as for the scope of the appended claims.

The invention claimed is:

1. A chemical process for recycling PET wastes, the process comprising the stages of: a) a saponification reaction stage, wherein PET waste particles are reacted with stoichiometric or excessive amounts of a strong base metal in an alcoholic reaction media that forms a single phase with ethylene glycol, which single phase is not miscible with an aqueous solution of a terephthalic acid salt, where the reaction is brought to the boiling temperature of the alcoholic reaction media and at atmospheric pressure, thereby obtaining as reaction products a salt of terephthalic acid with base metal and ethylene glycol, the latter being incorporated to the alcoholic reaction media; b) a separation stage of such terephthalic acid salt from the alcoholic reaction media comprising the steps of: i) cooling the reaction mixture to a temperature below 90° C.; ii) adding sufficient water to the reaction media in order to dissolve the terephthalic acid salt, thereby obtaining two phases, namely an aqueous phase where the terephthalic acid salt is dissolved, and an organic phase that consists of the alcoholic reaction media in which ethylene glycol is incorporated; and iii) a liquid-liquid separation phase, wherein the aqueous phase containing the terephthalic acid is separated from the organic phase; c) a terephthalic acid formation stage, wherein from terephthalic acid salt of stage (b) terephthalic acid is obtained, reacting said salt with a stronger acid than terephthalic acid to form and precipitate the latter as crystals; d) a solid-liquid separation stage, wherein precipitated terephthalic acid in stage (c) is separated from the media where it was crystallized; and e) an ethylene glycol recovery stage, wherein ethylene glycol and the alcoholic reaction media are separated and recovered from the reaction media separated in stage (b).

2. The chemical process for recycling PET wastes of claim 1, wherein the alcoholic reaction media is comprised of a monohydric alcohol selected from alcohols with 4 to 8, primary, secondary or tertiary, lineal or branched carbon atoms or a mixture thereof.

3. The chemical process for recycling PET wastes of claim 1, wherein the PET waste particles are obtained from any source and in any known shape.

4. The chemical process for recycling PET wastes of claim 1, wherein the base employed in the saponification reaction stage is selected from the group consisting in alkali metal hydroxides or alkaline-earth metal hydroxides.

5. The chemical process for recycling PET wastes of claim 4, wherein the base employed is sodium hydroxide (NaOH) or potassium hydroxide (KOH).

6. The chemical process for recycling PET wastes of claim 1, wherein in stage (c) of terephthalic acid formation, sulfuric acid concentrate or hydrochloric acid is employed until an acid pH is achieved in the media where this reaction takes place, thereby precipitating terephthalic acid crystals.

7. The chemical process for recycling PET wastes of claim 1, wherein in stage (d) of solid-liquid separation, terephthalic acid crystals are separated from the media where they were crystallized through a filtering process and then washed and purified.

8. The chemical process for recycling PET wastes of claim 1, wherein in stage (e) of ethylene glycol recovery, the alcoholic reaction media where ethylene glycol is incorporated undergoes a distillation process, thereby separating and recovering ethylene glycol from the alcoholic reaction media.

9. The chemical process for recycling PET wastes of claim 3, wherein the waste particles are obtained from used beverage bottles, packages, fibers, films, and other shapes.

* * * * *